US012788069B2

(12) United States Patent
Fard et al.

(10) Patent No.: US 12,788,069 B2
(45) Date of Patent: Nov. 10, 2026

(54) SMOKING SUBSTITUTE DEVICE

(71) Applicant: Imperial Tobacco Limited, Bristol (GB)

(72) Inventors: Daniel Fard, Liverpool (GB); Oliver Talbot, Liverpool (GB)

(73) Assignee: Imperial Tobacco Limited, Bristol (GB)

(*) Notice: Subject to any disclaimer, the term of this patent is extended or adjusted under 35 U.S.C. 154(b) by 0 days.

(21) Appl. No.: 18/639,467

(22) Filed: Apr. 18, 2024

(65) Prior Publication Data

US 2024/0265426 A1 Aug. 8, 2024

Related U.S. Application Data

(63) Continuation of application No. 17/002,185, filed on Aug. 25, 2020, now Pat. No. 11,989,756, which is a (Continued)

(30) Foreign Application Priority Data

Feb. 26, 2018 (GB) ..................................... 1803032

(51) Int. Cl.
*A24F 40/53* (2020.01)
*A24F 40/65* (2020.01)
(Continued)

(52) U.S. Cl.
CPC .............. *A24F 40/53* (2020.01); *A24F 40/65* (2020.01); *G06F 8/65* (2013.01); *G06Q 30/0269* (2013.01);
(Continued)

(58) Field of Classification Search
CPC ...... G06F 21/305; G06F 11/1433; G06F 8/65; A61B 5/0022; A61B 5/1112; H04L 67/34;
(Continued)

(56) References Cited

U.S. PATENT DOCUMENTS

2004/0103412 A1* 5/2004 Rao ........................... G06F 8/65 717/176
2007/0207800 A1* 9/2007 Daley ..................... H04W 8/22 455/425

(Continued)

FOREIGN PATENT DOCUMENTS

CN 106126293 A 11/2016
EP 3275324 A1 1/2018

(Continued)

OTHER PUBLICATIONS

Yu Bin, CN 103529988 (translation), Mar. 29, 2017, 8 pgs <CN_103529988.pdf>.*

(Continued)

*Primary Examiner* — Tuan A Vu
(74) *Attorney, Agent, or Firm* — DUNLAP CODDING, P.C.

(57) ABSTRACT

A computer implemented method, a smoking substitute device, a mobile device, and a remote server all for updating firmware of a smoking substitute device. The computer implemented method having the steps of: logging one or more errors encountered by the smoking substitute device; transmitting the one or more errors to a second device; selecting, based on the one or more errors encountered by the smoking substitute device, an updated firmware for use by a processor in the smoking substitute device; transmitting, from the second device to the smoking substitute device, the updated firmware; and updating the firmware of the smoking substitute device with the updated firmware received from the second device.

11 Claims, 5 Drawing Sheets

Related U.S. Application Data continuation of application No. PCT/EP2019/053508, filed on Feb. 13, 2019.

(51) Int. Cl.

| | |
|---|---|
| ***G06F 8/65*** | (2018.01) |
| ***G06Q 30/0251*** | (2023.01) |
| ***H04L 67/00*** | (2022.01) |
| *A24F 40/10* | (2020.01) |
| *A61B 5/00* | (2006.01) |
| *G06F 11/14* | (2006.01) |
| *G06F 21/30* | (2013.01) |

(52) U.S. Cl.

CPC .............. *H04L 67/34* (2013.01); *A24F 40/10* (2020.01); *A61B 5/0022* (2013.01); *G06F 11/1433* (2013.01); *G06F 21/305* (2013.01)

(58) Field of Classification Search

CPC .......... A24F 40/60; A24F 40/65; A24F 40/53; G06Q 30/0269; G06Q 20/20; H04W 8/22; G08C 17/02; H02H 3/042; H04M 15/00

See application file for complete search history.

(56) References Cited

U.S. PATENT DOCUMENTS

| | | | | |
|---|---|---|---|---|
| 2007/0268644 | A1* | 11/2007 | Schweitzer ............ | H02H 3/042 361/115 |
| 2009/0075641 | A1 | 3/2009 | Guven et al. | |
| 2009/0083060 | A1* | 3/2009 | Sherman ............... | H04M 15/00 455/550.1 |
| 2011/0167250 | A1* | 7/2011 | Dicks .................... | A61B 5/1112 713/2 |
| 2013/0013907 | A1* | 1/2013 | Marino ................. | G06F 21/305 713/2 |
| 2013/0159990 | A1 | 6/2013 | Bohrer et al. | |
| 2014/0028449 | A1* | 1/2014 | Sigal ...................... | G08C 17/02 340/12.5 |
| 2015/0007838 | A1 | 1/2015 | Fernando et al. | |
| 2018/0020724 | A1* | 1/2018 | Alarcon .................... | G06F 8/65 717/168 |
| 2018/0043114 | A1* | 2/2018 | Bowen .................... | A24F 40/65 |
| 2018/0107989 | A1* | 4/2018 | Fernando ............... | G06Q 20/20 |

FOREIGN PATENT DOCUMENTS

| | | | |
|---|---|---|---|
| WO | 2008048905 | A2 | 4/2008 |
| WO | WO 2016/173955 | A1 | 11/2016 |
| WO | WO 2017/055800 | A1 | 4/2017 |
| WO | WO 2017/205692 | A1 | 11/2017 |

OTHER PUBLICATIONS

International Search Report, mailed Jun. 3, 2019, in PCT/EP2019/053508, filed Feb. 13, 2019.

Written Opinion of the International Searching Authority, mailed Jun. 3, 2019, in PCT/EP2019/053508, filed Feb. 13, 2019.

UKIPO Search Report, dated Aug. 21, 2018, 6 pages.

* cited by examiner

SMOKING SUBSTITUTE DEVICE

CROSS-REFERENCE TO RELATED APPLICATIONS/INCORPORATION BY REFERENCE STATEMENT

The present patent application is a continuation of U.S. Ser. No. 17/002,185, filed on Aug. 25, 2020, which is a continuation of International Application No. PCT/EP2019/053508, filed Feb. 13, 2019; which claims priority to the patent application identified by GB Serial No. 1803032.0, filed on Feb. 26, 2018. The entire contents of each of the above-referenced patent(s)/patent application(s) are hereby expressly incorporated by reference herein.

TECHNICAL FIELD

The present invention relates to updating firmware used by a smoking substitute device and particularly, although not exclusively, to updating the firmware of a smoking substitute device based on errors logged relating to the smoking substitute device.

BACKGROUND

The smoking of tobacco is generally considered to expose a smoker to potentially harmful substances. It is generally thought that a significant amount of the potentially harmful substances are generated through the heat caused by the burning and/or combustion of the tobacco and the constituents of the burnt tobacco in the tobacco smoke itself.

Combustion of organic material such as tobacco is known to produce tar and other potentially harmful by-products. There have been proposed various smoking substitute devices in order to avoid the smoking of tobacco.

Such smoking substitute devices can form part of nicotine replacement therapies aimed at people who wish to stop smoking and overcome a dependence on nicotine.

Smoking substitute devices, which may also be known as electronic nicotine delivery systems, may comprise electronic systems that permit a user to simulate the act of smoking by producing an aerosol, also referred to as a "vapour", which is drawn into the lungs through the mouth (inhaled) and then exhaled. The inhaled aerosol typically bears nicotine and/or flavourings without, or with fewer of, the odour and health risks associated with traditional smoking.

In general, smoking substitute devices are intended to provide a substitute for the rituals of smoking, whilst providing the user with a similar experience and satisfaction to those experienced with traditional smoking and tobacco products.

The popularity and use of smoking substitute devices has grown rapidly in the past few years. Although originally marketed as an aid to assist habitual smokers wishing to quit tobacco smoking, consumers are increasingly viewing smoking substitute devices as desirable lifestyle accessories. Some smoking substitute devices are designed to resemble a traditional cigarette and are cylindrical in form with a mouthpiece at one end. Other smoking substitute devices do not generally resemble a cigarette (for example, the smoking substitute device may have a generally box-like form).

There are a number of different categories of smoking substitute devices, each utilising a different smoking substitute approach. A smoking substitute approach corresponds to the manner in which the substitute system operates for a user.

One approach for a smoking substitute device is the so-called "vaping" approach, in which a vapourisable liquid, typically referred to (and referred to herein) as "e-liquid", is heated by a heating device to produce an aerosol vapour which is inhaled by a user. An e-liquid typically includes a base liquid as well as nicotine and/or flavourings. The resulting vapour therefore typically contains nicotine and/or flavourings. The base liquid may include propylene glycol and/or vegetable glycerin.

A typical vaping smoking substitute device includes a mouthpiece, a power source (typically a battery), a tank for containing e-liquid, as well as a heating device. In use, electrical energy is supplied from the power source to the heating device, which heats the e-liquid to produce an aerosol (or "vapour") which is inhaled by a user through the mouthpiece.

Vaping smoking substitute devices can be configured in a variety of ways. For example, there are "closed system" vaping smoking substitute devices which typically have a sealed tank and heating element which is pre-filled with e-liquid and is not intended to be refilled by an end user. One subset of closed system vaping smoking substitute devices include a main body which includes the power source, wherein the main body is configured to be physically and electrically coupled to a consumable including the tank and the heating element. In this way, when the tank of a consumable has been emptied, the main body can be reused by connecting it to a new consumable. Another subset of closed system vaping smoking substitute devices are completely disposable, and intended for one-use only.

There are also "open system" vaping smoking substitute devices which typically have a tank that is configured to be refilled by a user, so the device can be used multiple times.

An example vaping smoking substitute device is the myblu™ e-cigarette. The myblu™ e-cigarette is a closed system device which includes a main body and a consumable. The main body and consumable are physically and electrically coupled together by pushing the consumable into the main body. The main body includes a rechargeable battery. The consumable includes a mouthpiece, a sealed tank which contains e-liquid, as well as a heating device, which for this device is a heating filament coiled around a portion of a wick which is partially immersed in the e-liquid. The device is activated when a microprocessor on board the main body detects a user inhaling through the mouthpiece. When the device is activated, electrical energy is supplied from the power source to the heating device, which heats e-liquid from the tank to produce a vapour which is inhaled by a user through the mouthpiece.

Another example vaping smoking substitute device is the blu PRO™ e-cigarette. The blu PRO™ e-cigarette is an open system device which includes a main body, a (refillable) tank, and a mouthpiece. The main body and tank are physically and electrically coupled together by screwing one to the other. The mouthpiece and refillable tank are physically coupled together by screwing one into the other, and detaching the mouthpiece from the refillable tank allows the tank to be refilled with e-liquid. The device is activated by a button on the main body. When the device is activated, electrical energy is supplied from the power source to a heating device, which heats e-liquid from the tank to produce a vapour which is inhaled by a user through the mouthpiece.

Another approach for a smoking substitute device is the so-called "heat not burn" ("HNB") approach in which tobacco (rather than e-liquid) is heated or warmed to release vapour. The tobacco may be leaf tobacco or reconstituted tobacco. The vapour may contain nicotine and/or flavourings. In the HNB approach the intention is that the tobacco is heated but not burned, i.e. does not undergo combustion.

A typical HNB smoking substitute device may include a main body and a consumable. The consumable may include the tobacco material. The main body and consumable may be configured to be physically coupled together. In use, heat may be imparted to the tobacco material by a heating device that is typically located in the main body, wherein airflow through the tobacco material causes moisture in the tobacco material to be released as vapour. A vapour may be formed from a carrier in the tobacco material (this carrier may for example include propylene glycol and/or vegetable glycerin) and additionally volatile compounds released from the tobacco. The released vapour may be entrained in the airflow drawn through the tobacco.

As the vapour passes through the smoking substitute device (entrained in the airflow) from an inlet to a mouthpiece (outlet), the vapour cools and condenses to form an aerosol (also referred to as a vapour) for inhalation by the user. The aerosol will normally contain the volatile compounds.

In HNB smoking substitute devices, heating as opposed to burning the tobacco material is believed to cause fewer, or smaller quantities, of the more harmful compounds ordinarily produced during smoking. Consequently, the HNB approach may reduce the odour and/or health risks that can arise through the burning, combustion and pyrolytic degradation of tobacco.

An example of the HNB approach is the IQOS® smoking substitute device from Philip Morris Ltd. The IQOS® smoking substitute device uses a consumable, including reconstituted tobacco located in a wrapper. The consumable includes a holder incorporating a mouthpiece. The consumable may be inserted into a main body that includes a heating device. The heating device has a thermally conductive heating knife which penetrates the reconstituted tobacco of the consumable, when the consumable is inserted into the heating device. Activation of the heating device heats the heating element (in this case a heating knife), which, in turn, heats the tobacco in the consumable. The heating of the tobacco causes it to release nicotine vapour and flavourings which may be drawn through the mouthpiece by the user through inhalation.

A second example of the HNB approach is the device known as "Glo"® from British American Tobacco p.l.c. Glo® comprises a relatively thin consumable. The consumable includes leaf tobacco which is heated by a heating device located in a main body. When the consumable is placed in the main body, the tobacco is surrounded by a heating element of the heating device. Activation of the heating device heats the heating element, which, in turn, heats the tobacco in the consumable. The heating of the tobacco causes it to release nicotine vapour and flavourings which may be drawn through the consumable by the user through inhalation. The tobacco, when heated by the heating device, is configured to produce vapour when heated rather than when burned (as in a smoking apparatus, e.g. a cigarette). The tobacco may contain high levels of aerosol formers (carrier), such as vegetable glycerine ("VG") or propylene glycol ("PG").

The present inventor(s) have observed that most smoking substitute devices currently on the market are configured to operate in isolation of other devices, which limits the functions the smoking substitute devices can perform.

The present invention has been devised in light of the above considerations.

BRIEF DESCRIPTION OF THE DRAWINGS

Embodiments and experiments illustrating the principles of the invention will now be discussed with reference to the accompanying figures in which:

FIG. 2(*b*) shows the main body of the smoking substitute device of FIG. 2(*a*) without the consumable;

FIG. 2(*c*) shows the consumable of the smoking substitute device of FIG. 2(*a*) without the main body;

FIG. 3(*b*) is a schematic view of the consumable of the smoking substitute device of FIG. 2(*a*);

DETAILED DESCRIPTION

Figure 1:
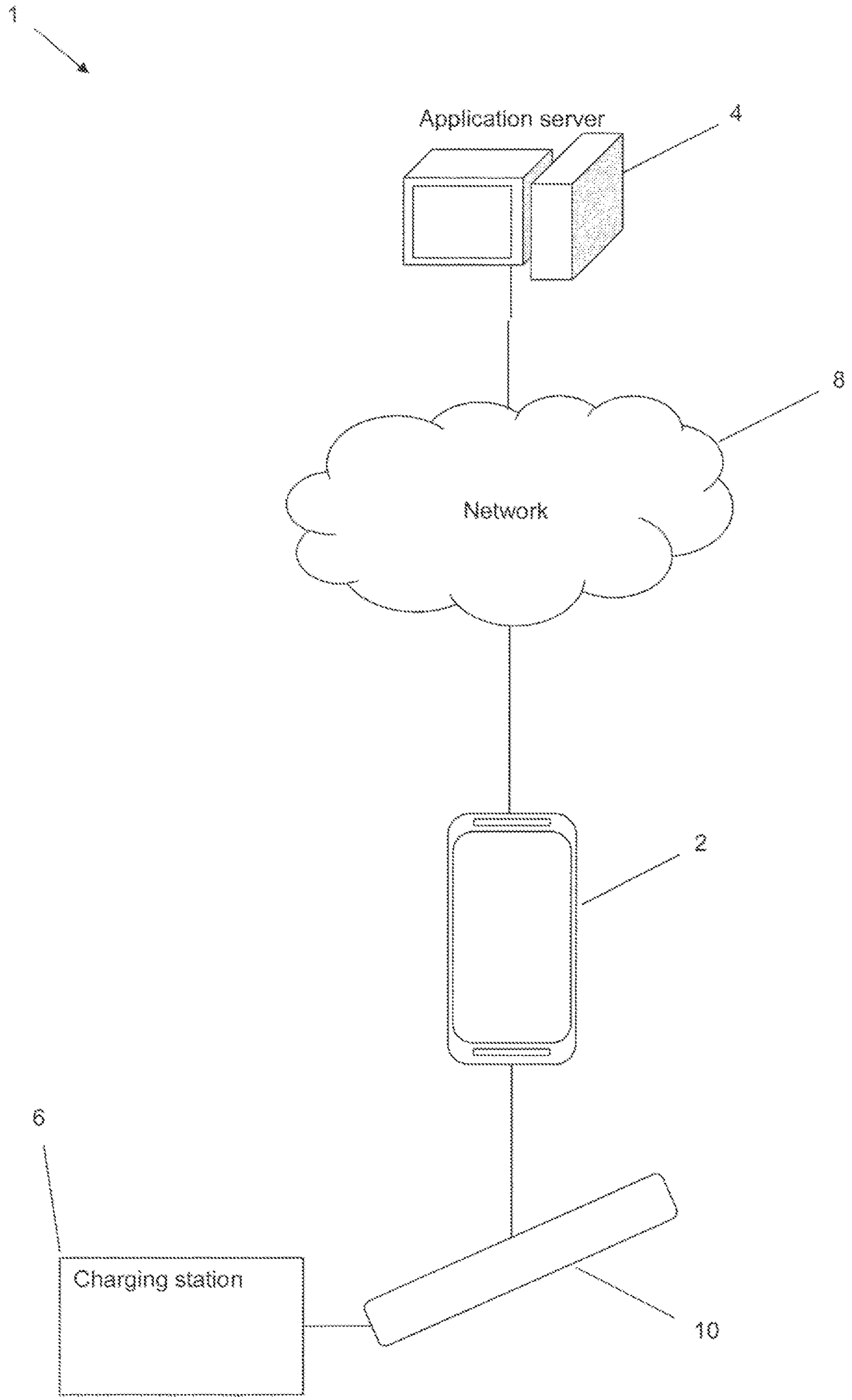
FIG. 1 shows an example system for managing a smoking substitute device.

At their most general, some aspects of the invention provide for the updating of firmware of a smoking substitute device based on one or more errors encountered by the smoking substitute device.

Accordingly, in a first aspect, the invention provides a computer implemented method for updating firmware of a smoking substitute device, having the steps of: logging one or more errors encountered by the smoking substitute device; transmitting the one or more errors to a second device; selecting, based on the one or more errors encountered by the smoking substitute device, an updated firmware for use by a processor in the smoking substitute device; transmitting, from the second device to the smoking substitute device, the updated firmware; and updating the firmware of the smoking substitute device with the updated firmware received from the second device.

Advantageously, firmware which is able to prevent or ameliorate at least some of the one or more errors can be provided to the smoking substitute device autonomously.

The errors may be logged by the smoking substitute device into memory of smoking substitute device.

The second device may be a mobile device which is connected to the smoking substitute device and the logged errors are transmitted to the mobile device. The second device may be a remote server, e.g. as discussed below.

The updated firmware may be selected from a store of firmware stored in a memory of the second device.

The step of "selecting" may be taken to imply the existence of multiple items of firmware suitable for use in the smoking substitute device, e.g. with one of these multiple items of firmware suitable for use in the smoking substitute device being selected as the updated firmware for use by the (processor in the) smoking substitute device based on the one or more errors encountered by the smoking substitute device.

Thus, the store of firmware stored in the memory of the second device may store multiple items of firmware suitable for use in the smoking substitute device, e.g. with one of these multiple items of firmware suitable for use in the smoking substitute device being selected as the updated firmware for use by the (processor in the) smoking substitute device based on the one or more errors encountered by the smoking substitute device.

The store of firmware stored in the second device may be periodically updated by a remote server.

The mobile device may select the updated firmware from a store of firmware stored in memory of the mobile device.

Alternatively or additionally the logged errors may be subsequently transmitted from the mobile device to a remote server to which the mobile device is connected. The remote server may select the updated firmware from a store of firmware stored in memory of the remote server, and the remote server may transmit the selected updated firmware to the mobile device.

The logged one or more errors may include an indication of the number of times that the smoking substitute device failed to connect to the mobile device within a given period. The server (or mobile device) may determine that a timeout period for connection as set in the smoking substitute device is too short. The remote server (or mobile device) may select an updated firmware configured to address the failure to connect.

Updating the firmware of the smoking substitute device may include overwriting a firmware-storing portion of memory of the smoking substitute device with the updated firmware.

The one or more errors may include any one or more of: a measurement of the voltage of a battery in the smoking substitute device; a measurement of the resistance of a coil in the smoking substitute device; an indication of the number of times a consumable is inserted into the smoking substitute device within a given period; an indication of the number of times that the smoking substitute device has failed to connect to a mobile device within a given period; an indication that there is an issue with charging a battery within the smoking substitute device; and an indication that a pressure within the smoking substitute device has dropped.

In a second aspect, the invention provides a smoking substitute device including a processor and memory, wherein the memory includes instructions which cause the processor to: log one or more error(s) encountered by the smoking substitute device; transmit the one or more errors to a second device; receive from the second device an updated firmware for use by the processor of the smoking substitute device, where the updated firmware is selected based on the one or more error(s) encountered by the smoking substitute device; and update firmware of the smoking substitute device with the updated firmware received from the second device.

Advantageously, firmware which is able to prevent or ameliorate at least some of the one or more errors can be provided to the smoking substitute device autonomously.

The second device may be a mobile device which is connected to the smoking substitute device and the logged errors are transmitted to the mobile device.

The second device may be a remote server, e.g. as discussed below.

The updated firmware may be selected from a store of firmware stored in a memory of the second device.

The step of "selecting" may be taken to imply the existence of multiple items of firmware suitable for use in the smoking substitute device, e.g. with one of these multiple items of firmware suitable for use in the smoking substitute device being selected as the updated firmware for use by the (processor in the) smoking substitute device based on the one or more errors encountered by the smoking substitute device.

Thus, the store of firmware stored in the memory of the second device may store multiple items of firmware suitable for use in the smoking substitute device, e.g. with one of these multiple items of firmware suitable for use in the smoking substitute device being selected as the updated firmware for use by the (processor in the) smoking substitute device based on the one or more errors encountered by the smoking substitute device.

The store of firmware stored in the second device may be periodically updated by a remote server.

The mobile device may select the updated firmware from a store of firmware stored in memory of the mobile device.

Alternatively or additionally, the logged errors may subsequently be transmitted from the mobile device to a remote server to which the mobile device is connected. The remote server may select the updated firmware from a store of firmware stored in memory of the remote server, and the remote server may transmit the selected updated firmware to the mobile device.

The logged one or more errors may include an indication of the number of times that the smoking substitute device failed to connect to the mobile device within a given period. The server (or mobile device) may determine that a timeout period for connection as set in the smoking substitute device is too short. The remote server (or mobile device) may select an updated firmware configured to address the failure to connect.

Updating the firmware of the smoking substitute device may include overwriting a firmware-containing portion of memory of the smoking substitute device.

The one or more errors may include any one or more of: a measurement of the voltage of a battery in the smoking substitute device; a measurement of the resistance of a coil in the smoking substitute device; an indication of the number of times a consumable is inserted into the smoking substitute device within a given period; an indication of the number of times that the smoking substitute device has failed to connect to a mobile device within a given period; an indication that there is an issue with charging a battery within the smoking substitute device; and an indication that a pressure within the smoking substitute device has dropped.

The second aspect may provide a system including the smoking substitute device.

The system may additionally include a mobile device as described herein (e.g. as described in connection with the first aspect of the invention). The system may additionally include a remote server as described herein (e.g. as described in connection with the first aspect of the invention).

In a third aspect, the invention provides a mobile device, including a processor and memory, wherein the memory includes instructions which cause the processor to: receive from a smoking substitute device one or more error(s) encountered by the smoking substitute device; either (i) or (ii): (i) select, based on the received one or more error(s), an updated firmware for use by a processor of the smoking substitute device, or (ii) transmit the received one or more error(s) to a remote server, and receive from the remote server an updated firmware for use by the processor of the smoking substitute device, where the updated firmware is selected based on the one or more error(s) encountered by the smoking substitute device; and transmit the updated firmware to the smoking substitute device for use in updating firmware of the smoking substitute device.

Advantageously, firmware which is able to prevent or ameliorate at least some of the one or more errors can be provided to the smoking substitute device autonomously.

The error(s) received from the smoking substitute device may be errors which have been logged by the smoking substitute device into memory of the smoking substitute device.

The mobile device may select the updated firmware from a store of firmware stored in memory of the mobile device.

The step of "selecting" may be taken to imply the existence of multiple items of firmware suitable for use in the smoking substitute device, e.g. with one of these multiple items of firmware suitable for use in the smoking substitute device being selected as the updated firmware for use by the (processor in the) smoking substitute device based on the one or more errors encountered by the smoking substitute device.

Thus, the store of firmware stored in the memory of the mobile device may store multiple items of firmware suitable for use in the smoking substitute device, e.g. with one of these multiple items of firmware suitable for use in the smoking substitute device being selected as the updated firmware for use by the (processor in the) smoking substitute device based on the one or more errors encountered by the smoking substitute device.

The remote server may select the updated firmware from a store of firmware stored in memory of the remote server.

Updating the firmware of the smoking substitute device may include sending instructions to the smoking substitute device which cause it to overwrite a firmware-storing portion of memory of the smoking substitute device with the updated firmware.

The one or more errors may include any one or more of: a measurement of the voltage of a battery in the smoking substitute device; a measurement of the resistance of a coil in the smoking substitute device; an indication of the number of times a consumable is inserted into the smoking substitute device within a given period; an indication of the number of times that the smoking substitute device has failed to connect to a mobile device within a given period; an indication that there is an issue with charging a battery within the smoking substitute device; and an indication that a pressure within the smoking substitute device has dropped.

In a fourth aspect, the invention provides a remote server, including a processor and memory, wherein the memory includes instructions which cause the processor to: receive, directly or indirectly, one or more error(s) encountered by a smoking substitute device; select, based on the one or more error(s), an updated firmware for use by a processor of the smoking substitute device; and transmit, directly or indirectly, the selected updated firmware to the smoking substitute device for use in updating the firmware of the smoking substitute device.

Advantageously, firmware which is able to prevent or ameliorate at least some of the one or more errors can be provided to the smoking substitute device autonomously.

The error(s) received from the smoking substitute device may be errors which have been logged by the smoking substitute device into memory of the smoking substitute device. By directly, it may be meant that the smoking substitute device forms its own connection to the remote server. By indirectly, it may be meant that the smoking substitute device forms a connection to a further device (e.g. a mobile device), said further device then forming its own connection to the remote server.

The remote server may select the updated firmware from a store of firmware stored in memory of the remote server.

The step of "selecting" may be taken to imply the existence of multiple items of firmware suitable for use in the smoking substitute device, e.g. with one of these multiple items of firmware suitable for use in the smoking substitute device being selected as the updated firmware for use by the (processor in the) smoking substitute device based on the one or more errors encountered by the smoking substitute device.

Thus, the store of firmware stored in the memory of the remote server may store multiple items of firmware suitable for use in the smoking substitute device, e.g. with one of these multiple items of firmware suitable for use in the smoking substitute device being selected as the updated firmware for use by the (processor in the) smoking substitute device based on the one or more errors encountered by the smoking substitute device.

Updating the firmware of the smoking substitute device may include sending instructions to the smoking substitute device which cause it to overwrite a firmware-storing portion of memory of the smoking substitute device with the updated firmware.

In a fifth aspect, the invention provides a computer implemented method for updating firmware of a smoking substitute device, having the steps of: connecting the smoking substitute device to an application running on a mobile device, said application communicating with a processor of the smoking substitute device; retrieving by the application on the mobile device, over-the-air, an updated firmware for use by the processor in the smoking substitute device; transmitting the updated firmware from the application on the mobile device to the smoking substitute device; and updating the firmware on the smoking substitute device using the updated firmware.

In a sixth aspect, the invention provides a mobile device including a processor and memory, the memory containing instructions which cause the processor to: form a network connection to a processor of a smoking substitute device; retrieve, over-the-air, an updated firmware for use by the processor in the smoking substitute device; transmit the updated firmware to the smoking substitute device; and instruct the smoking substitute device to update the firmware on the smoking substitute device using the updated firmware.

The invention includes the combination of the aspects and preferred features described except where such a combination is clearly impermissible or expressly avoided. Thus, any one or more steps or features described in connection with any one aspect of the invention may be incorporated into any other aspect of the invention.

Aspects and embodiments of the present invention will now be discussed with reference to the accompanying figures. Further aspects and embodiments will be apparent to those skilled in the art. All documents mentioned in this text are incorporated herein by reference.

FIG. 1 shows an example system 1 for managing a smoking substitute device 10.

The system 1 as shown in FIG. 1 includes a mobile device 2, an application server 4, an optional charging station 6, as well as the smoking substitute device 10.

The smoking substitute device 10 is configured to communicate wirelessly, e.g. via Bluetooth®, with an application (or "app") installed on the mobile device 2, e.g. via a suitable wireless interface (not shown) on the mobile device 2. The smoking substitute device 10 may, some examples, be configured to communicate wirelessly with the application server directly (i.e. not via mobile device 2). The mobile device 2 may be a mobile phone, for example. The application on the mobile phone is configured to communicate with the application server 4, via a network 8. The application server 4 may utilise cloud storage, for example.

The network 8 may include a cellular network and/or the internet.

A skilled person would readily appreciate that the mobile device 2 may be configured to communicate via the network 8 according to various communication channels, preferably a wireless communication channel such as via a cellular network (e.g. according to a standard protocol, such as 3G or 4G) or via a WiFi® network.

The app installed on the mobile device and the application server 4 may be configured to assist a user with their smoking substitute device 10, based on information communicated between the smoking substitute device 10 and the app and/or information communicated between the app and the application server 4.

The charging station 6 (if present) may be configured to charge (and optionally communicate with) the smoking substitute device 10, via a charging port on the smoking substitute device 10. The charging port on the smoking substitute device 10 may be a USB port, for example, which may allow the smoking substitute device to be charged by any USB-compatible device capable of delivering power to the smoking substitute device 10 via a suitable USB cable (in this case the USB-compatible device would be acting as the charging station 6). Alternatively, the charging station could be a docking station specifically configured to dock with the smoking substitute device 10 and charge the smoking substitute device 10 via the charging port on the smoking substitute device 10.

Figure 2A:
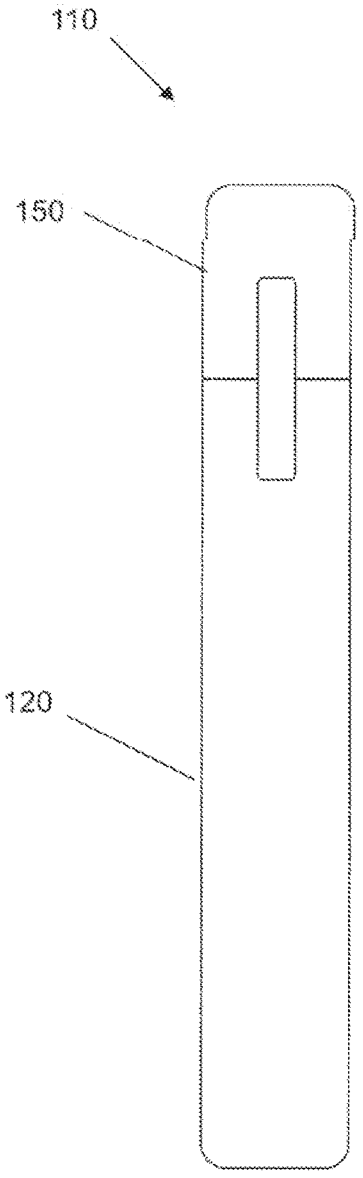
FIG. 2(*a*) shows an example smoking substitute device for use as the smoking substitute device in the system of FIG. 1.
Figure 2B:
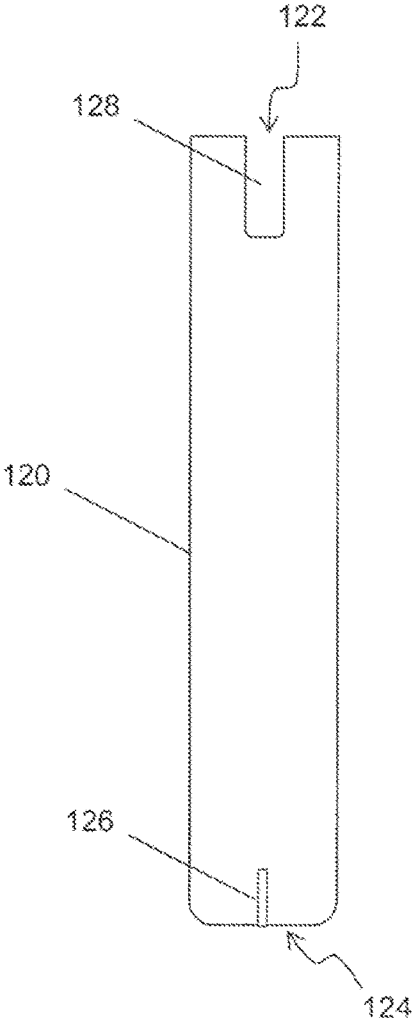
Figure 2C:
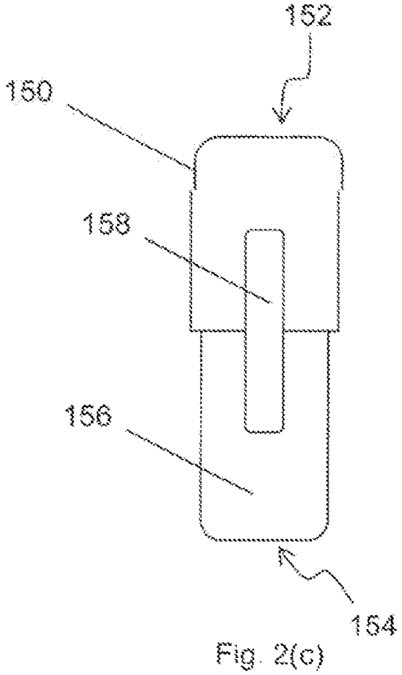

FIG. 2(*a*) shows an example smoking substitute device 110 for use as the smoking substitute device 10 in the system 1 of FIG. 1.

In this example, the smoking substitute device 110 includes a main body 120 and a consumable 150. The consumable 150 may alternatively be referred to as a "pod".

In this example, the smoking substitute device 110 is a closed system vaping device, wherein the consumable 150 includes a sealed tank 156 and is intended for one-use only.

FIG. 2(*a*) shows the smoking substitute device 110 with the main body 120 physically coupled to the consumable 150.

FIG. 2(*b*) shows the main body 120 of the smoking substitute device 110 without the consumable 150.

FIG. 2(*c*) shows the consumable 150 of the smoking substitute device 110 without the main body 120.

The main body 120 and the consumable 150 are configured to be physically coupled together, in this example by pushing the consumable 150 into an aperture in a top end 122 of the main body 120. In other examples, the main body 120 and the consumable could be physically coupled together by screwing one onto the other, or through a bayonet fitting, for example. An optional light 126, e.g. an LED located behind a small translucent cover, is located a bottom end 124 of the main body 120. The light 126 may be configured to illuminate when the smoking substitute device 110 is activated.

The consumable 150 includes a mouthpiece (not shown) at a top end 152 of the consumable 150, as well as one or more air inlets (not shown in FIG. 2) so that air can be drawn into the smoking substitute device 110 when a user inhales through the mouthpiece. At a bottom end 154 of the consumable 150, there is located a tank 156 that contains e-liquid. The tank 156 may be a translucent body, for example.

The tank 156 preferably includes a window 158, so that the amount of e-liquid in the tank 156 can be visually assessed. The main body 120 includes a slot 128 so that the window 158 of the consumable 150 can be seen whilst the rest of the tank 156 is obscured from view when the consumable 150 is inserted into the aperture in the top end 122 of the main body 120.

The tank 156 may be referred to as a "clearomizer" if it includes a window 158, or a "cartomizer" if it does not.

Figure 3A:
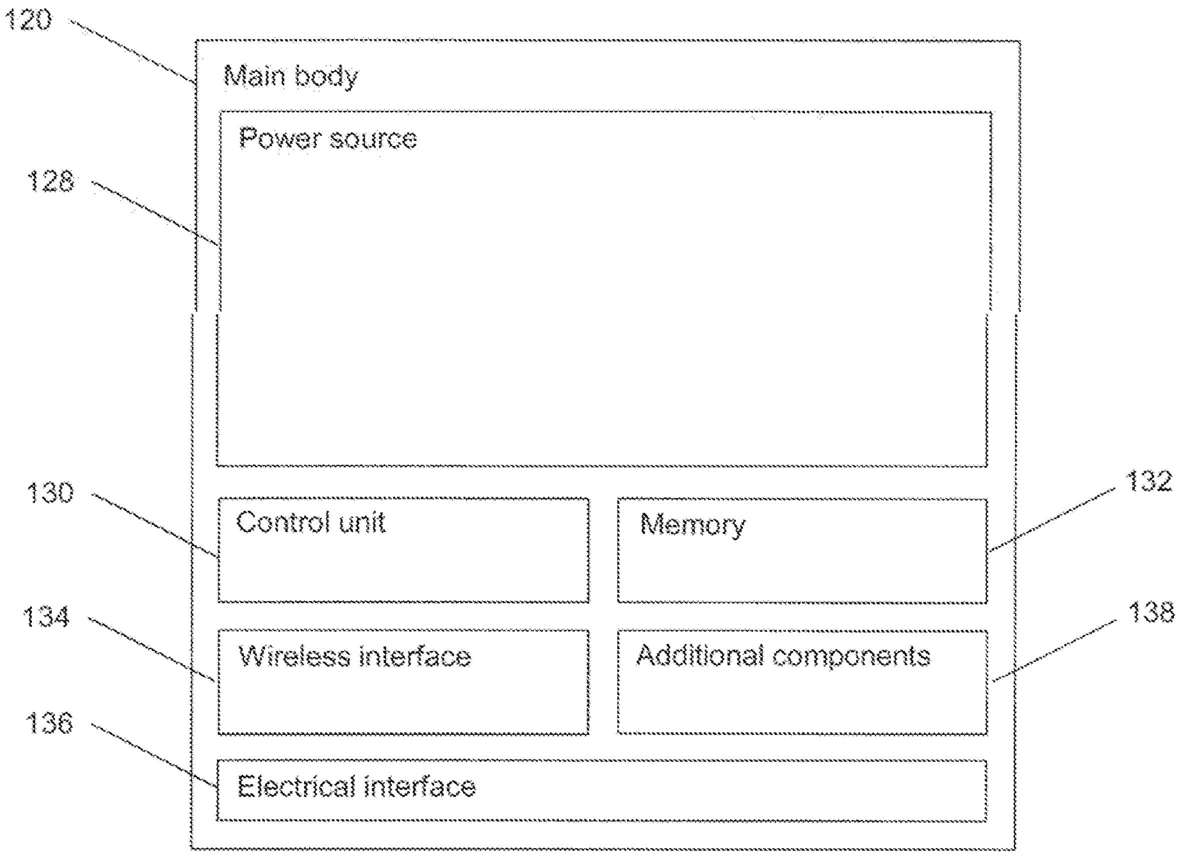
FIG. 3(*a*) is a schematic view of the main body of the smoking substitute device of FIG. 2(*a*)
Figure 3B:
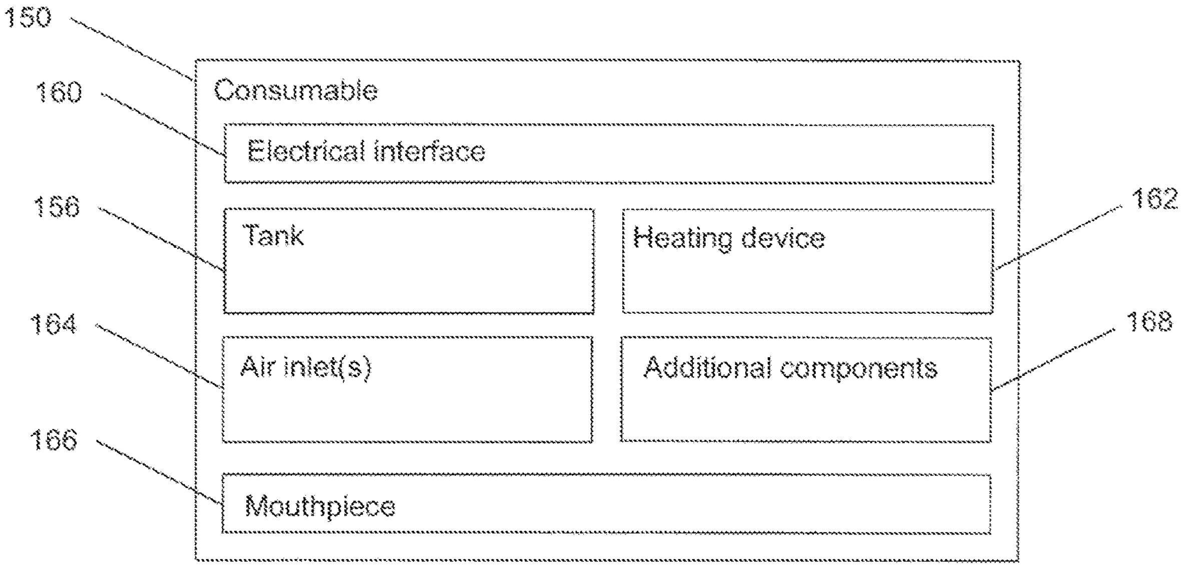

FIG. 3(*a*) is a schematic view of the main body 120 of the smoking substitute device 110.

FIG. 3(*b*) is a schematic view of the consumable 150 of the smoking substitute device 110.

As shown in FIG. 3(*a*), the main body 120 includes a power source 128, a control unit 130, a memory 132, a wireless interface 134, an electrical interface 136, and, optionally, one or more additional components 138.

The power source 128 is preferably a battery, more preferably a rechargeable battery.

The control unit 130 may include a microprocessor, for example.

The control unit 130 may be configured to log one or more errors in the memory 132 of the smoking substitute device.

For example, the control unit may be configured to log any one or more of: a measurement of the voltage of the power source (e.g. a battery) in the smoking substitute device; a measurement of the resistance of a coil in the smoking substitute device; an indication of the number of times a consumable is inserted into the smoking substitute device within a given period; an indication of the number of times that the smoking substitute device has failed to connect to a mobile device within a given period; an indication that there is an issue with charging a battery within the smoking substitute device; and an indication that a pressure (e.g. air pressure) within the smoking substitute device has dropped.

The memory 132 is preferably includes non-volatile memory. The memory may include instructions which, when implemented, cause the control unit 130 to perform certain tasks or steps of a method.

The wireless interface 134 is preferably configured to communicate wirelessly with the mobile device 2, e.g. via Bluetooth®. To this end, the wireless interface 134 could include a Bluetooth® antenna. Other wireless communication interfaces, e.g. WiFi®, are also possible. As discussed above, the wireless interface 134 may be configured to communicate wirelessly with the remote server 2.

The electrical interface 136 of the main body 120 may include one or more electrical contacts. The electrical interface 136 may be located in, and preferably at the bottom of, the aperture in the top end 122 of the main body 120. When the main body 120 is physically coupled to the consumable 150, the electrical interface 136 may be configured to pass electrical power from the power source 128 to (e.g. a heating device of) the consumable 150 when the smoking substitute device 110 is activated, e.g. via the electrical interface 160 of the consumable 150 (discussed below). When the main body 120 is not physically coupled to the consumable 150, the electrical interface may be configured to receive power from the charging station 6.

The additional components 138 of the main body 120 may include the optional light 126 discussed above.

The additional components 138 of the main body 120 may, if the power source 128 is a rechargeable battery, include a charging port configured to receive power from the charging station 6. This may be located at the bottom end 124 of the main body 120. Alternatively, the electrical interface 136 discussed above is configured to act as a charging port configured to receive power from the charging station 6 such that a separate charging port is not required.

The additional components 138 of the main body 120 may, if the power source 128 is a rechargeable battery, include a battery charging control circuit, for controlling the charging of the rechargeable battery. However, a battery charging control circuit could equally be located in the charging station 6 (if present).

The additional components 138 of the main body 120 may include an airflow sensor for detecting airflow in the smoking substitute device 110, e.g. caused by a user inhaling through a mouthpiece 166 (discussed below) of the smoking substitute device 110. The smoking substitute device 110 may be configured to be activated when airflow is detected by the airflow sensor. This optional sensor could alternatively be included in the consumable 150 (though this is less preferred where the consumable 150 is intended to be disposed of after use, as in this example).

The additional components 138 of the main body 120 may include an actuator, e.g. a button. The smoking substitute device 110 may be configured to be activated when the actuator is actuated. This provides an alternative to the airflow sensor noted, as a mechanism for activating the smoking substitute device 110.

As shown in FIG. 3(*b*), the consumable 150 includes the tank 156, an electrical interface 160, a heating device 162, one or more air inlets 164, a mouthpiece 166, and, optionally, one or more additional components 168.

The electrical interface 160 of the consumable 150 may include one or more electrical contacts. The electrical interface 136 of the main body 120 and an electrical interface 160 of the consumable 150 are preferably configured to contact each other and therefore electrically couple the main body 120 to the consumable 150 when the main body 120 is physically coupled to the consumable 150. In this way, electrical energy (e.g. in the form of an electrical current) is able to be supplied from the power source 128 in the main body 120 to the heating device 162 in the consumable 150.

The heating device 162 is preferably configured to heat e-liquid contained in the tank 156, e.g. using electrical energy supplied from the power source 128. In one example, the heating device 162 may include a heating filament and a wick, wherein a first portion of the wick extends into the tank 156 in order to draw e-liquid out from the tank 156, and wherein the heating filament coils around a second portion of the wick located outside the tank 156. In this example, the heating filament is configured to heat up e-liquid drawn out of the tank 156 by the wick to produce an aerosol vapour.

The one or more air inlets 164 are preferably configured to allow air to be drawn into the smoking substitute device 110, when a user inhales through the mouthpiece 166.

In use, a user activates the smoking substitute device 110, e.g. through actuating an actuator included in the main body 120 or by inhaling through the mouthpiece 166 as described above. Upon activation, the control unit 130 may supply electrical energy from the power source 128 to the heating device 162 (via electrical interfaces 136, 166), which may cause the heating device 162 to heat e-liquid drawn from the tank 156 to produce a vapour which is inhaled by a user through the mouthpiece 166.

Of course, a skilled reader would readily appreciate that the smoking substitute device 110 shown in FIGS. 2 and 3 shows just one example implementation of a smoking substitute device, and that other forms of smoking substitute device could be used as the smoking substitute device 10 of FIG. 1.

By way of example, a HNB smoking substitute device including a main body and a consumable could be used as the smoking substitute device 10 of FIG. 1, instead of the smoking substitute device 110. One such HNB smoking substitute device is the IQOS™ smoking substitute device discussed above.

As another example, an open system vaping device which includes a main body, a refillable tank, and a mouthpiece could be used as the smoking substitute device 10 of FIG. 1, instead of the smoking substitute device 110. One such open system vaping device is the blu PRO™ e-cigarette discussed above.

As another example, an entirely disposable (one use) smoking substitute device could be used as the smoking substitute device 10 of FIG. 1, instead of the smoking substitute device 110.

Figure 4:
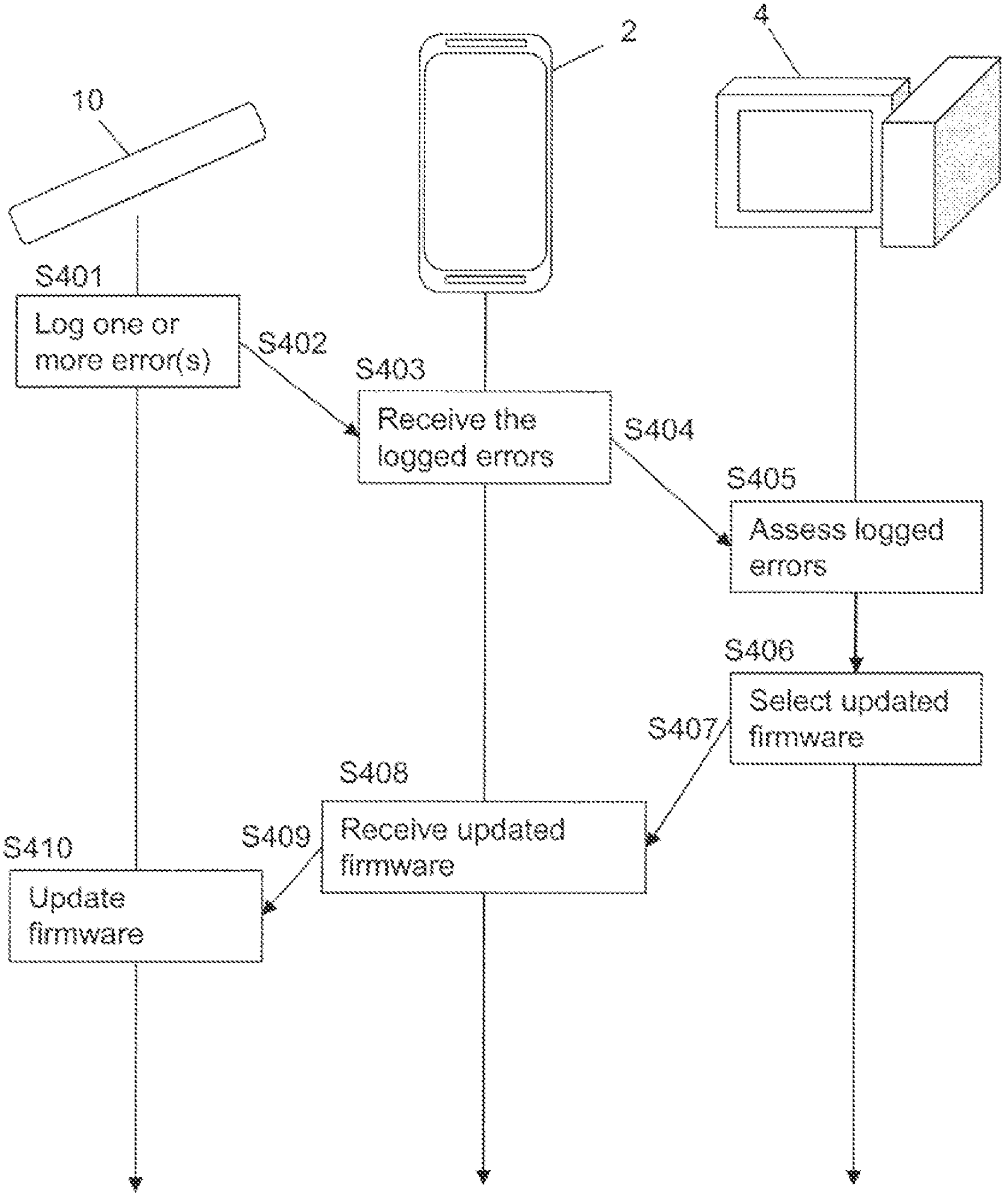
FIG. 4 is a network flow diagram illustrating a method according to the present invention.

FIG. 4 illustrates a method according to the present invention. The figure is a data flow diagram, where time is presented along the long (vertical) axis.

In a first step, S401, one or more error(s) are logged by the smoking substitute device 10. As has been discussed previously, the one or more error(s) may be logged in different ways. For example, the control unit 130 of the smoking substitute device may be configured to note and store in memory 132 a measurement of the voltage of the battery 128 or the resistance of a coil in the smoking substitute device.

In this embodiment, in step S402, the logged errors are transmitted to the mobile device 2. They are the received and held in memory of the mobile device in step S403. Subsequently, the logged errors are transmitted in step S404 to the remote server 4.

The remote server then, in step S405, assess the logged errors. By assessing, it may be meant that the server ascribes a fault in the smoking substitute device to the one or more logged errors. For example, if the logged error was an indication of the number of times that the smoking substitute device failed to connect to the mobile device within a given period, the server may ascertain that a timeout period for connection as set in the smoking substitute device is too short.

As a result of this assessment, the remote server then selects (in step S406) an updated firmware (e.g. from a store of firmware stored in a memory of the remote server, e.g. wherein the store of firmware stores multiple items of firmware suitable for use in the smoking substitute device 10) which aims to address (e.g. is configured to address) the faults (e.g. the one or more logged errors) identified in the smoking substitute device. This selected firmware is then transmitted in step S407 to the mobile device 2. The mobile device, in step S408, receives the updated firmware. Here the mobile device may also verify that the updated firmware is compatible with the smoking substitute device to which it is connected and may prompt a user of the mobile device asking for authorisation to update the firmware on the smoking substitute device.

The updated firmware is then transmitted, in step S409, to the smoking substitute device 10. Next, in step S410, the smoking substitute device then updates the firmware contained in a firmware-storing portion of memory. This updating may involve overwriting the existing firmware with the updated firmware.

In this embodiment, the logged errors are transmitted first to the mobile device 2 and then on to the remote server 4. However, as described above, it is possible that the smoking substitute device 10 forms a connection to the remote server 4 without going via the mobile device 2. For example, if the smoking substitute device included a WiFi® adapter or cellular network adapter.

In a different embodiment, logged errors are transmitted to the mobile device 2 from the smoking substitute device 10 and are not then passed on to the remote server 4. In this embodiment, the mobile device 2 includes a store of updated firmware and selects, based on an assessment of the logged errors performed by the mobile device, which of an updated firmware from the store of updated firmware to send to the smoking substitute device (e.g. wherein the store of firmware stores multiple items of firmware suitable for use in the smoking substitute device 10). In this embodiment, the remote server 4 may periodically update the store of updated firmware on the mobile device either by pushing updated to the mobile device or in response to polls from the mobile device.

Figure 5:
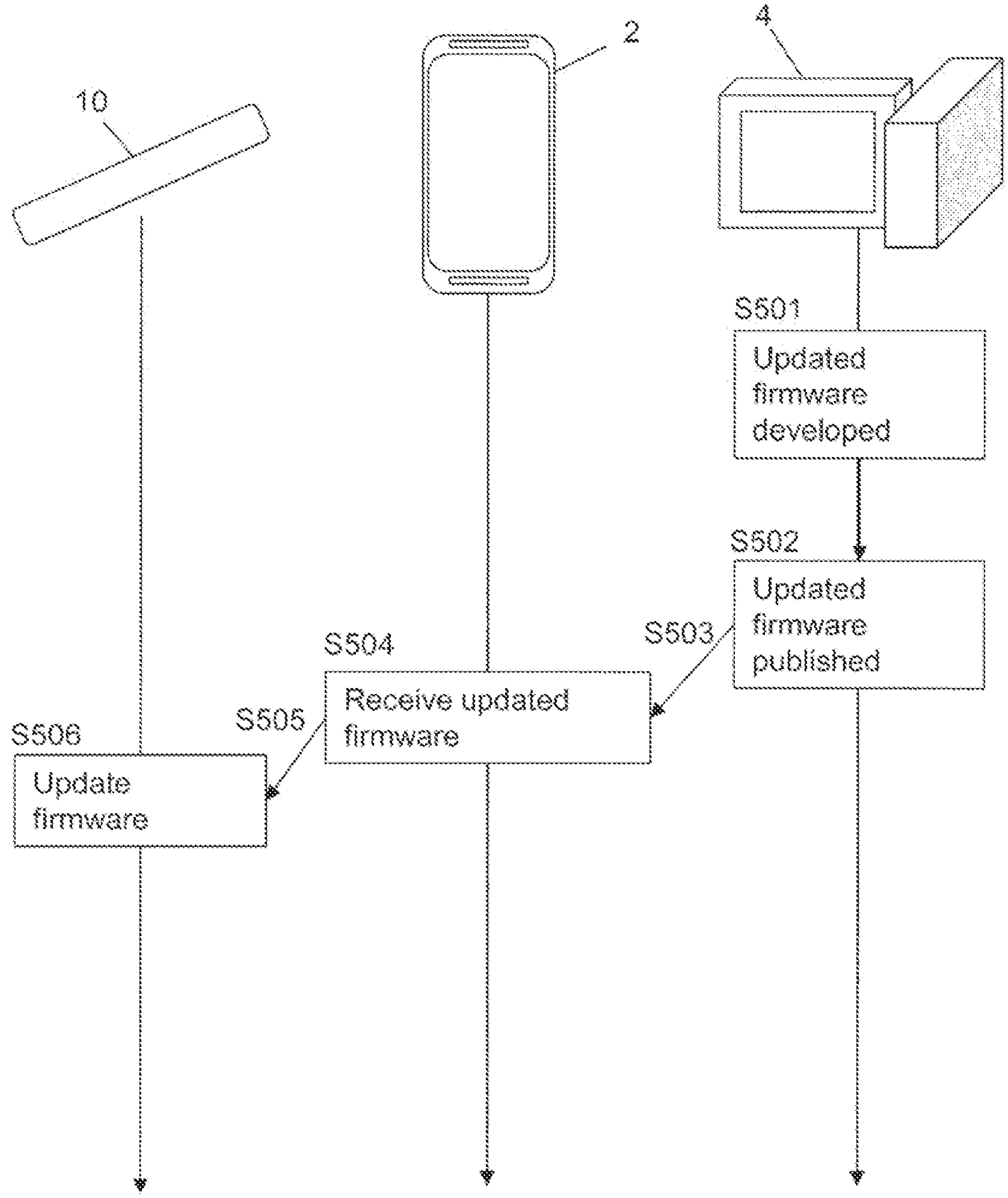
FIG. 5 is a network flow diagram illustrating a method according to the present invention.

FIG. 5 illustrates a method according to the present invention. This figure is a data flow diagram, where time is presented along the long (vertical) axis.

In a first step, S501, updated firmware is developed and stored on the remote server 4. Subsequently, as shown in S502, the updated firmware is published and so it can be seen by mobile device 2. In one embodiment, information indicating the publication firmware may be pushed to the mobile device actively. In an alternative embodiment, the mobile device may periodically poll the remote server to see if new firmware is available. The user of the mobile device may instigate a poll at any time.

Either as a push, or in response to a poll, the remote server 4 sends the updated firmware to the mobile device in step S503. The mobile device then receives the updated firmware in step S504. As discussed above, the mobile device may also verify that the updated firmware is compatible with the smoking substitute device to which it is connected and may prompt a user of the mobile device asking for authorisation to update the firmware on the smoking substitute device.

This updated firmware may, in addition to correcting generic errors which the developers are aware of, provide new features on the smoking substitute device.

In this embodiment, the updated firmware is transmitted from the remote server 4 to the smoking substitute device 10 via the mobile device 2. However, as described above, it is possible that the smoking substitute device 10 forms a connection to the remote server 4 without going via the mobile device 2. For example, if the smoking substitute device 10 included a WiFi® adapter or cellular network adapter.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

Throughout this specification, including the claims which follow, unless the context requires otherwise, the word "connect" and "connected" should be understood to express a networked connection between one device and another which is can be either direct or indirect (via intermediary).

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the adverb "about," it will be understood that the particular value forms another embodiment. The term "about" in relation to a numerical value is optional and means for example +/−10%.

The invention claimed is:

1. A computer implemented method for updating firmware of a smoking substitute device, the method comprising the steps of:

logging, by the smoking substitute device, one or more errors encountered by the smoking substitute device;

transmitting the one or more errors to a mobile device, wherein the mobile device is connected to the smoking substitute device;

the mobile device assessing the one or more errors encountered by the smoking substitute device by ascribing a fault in the smoking substitute device to the one or more logged errors;

the mobile device selecting, from a store of multiple items of firmware suitable for use in the smoking substitute device, based on the assessing performed by the mobile device, an updated firmware for use by a processor in the smoking substitute device to address the one or more errors encountered by the smoking substitute device;

transmitting, from the mobile device to the smoking substitute device, the updated firmware; and updating the firmware of the smoking substitute device with the updated firmware received from the mobile device to prevent or ameliorate at least some of the one or more errors in future use of the smoking substitute device.

2. The method of claim 1, wherein the errors are logged by the smoking substitute device into memory of the smoking substitute device.

3. The method of claim 1, wherein the mobile device selects the updated firmware from a store of firmware stored in memory of the mobile device.

4. The method of claim 1, wherein the store of firmware stored in the memory of the mobile device is periodically updated by a remote server.

5. The method of claim 1, wherein the logged errors are subsequently transmitted from the mobile device to a remote server to which the mobile device is connected.

6. The method of claim 1, wherein updating the firmware of the smoking substitute device includes overwriting a firmware-storing portion of memory of the smoking substitute device with the updated firmware.

7. The method of claim 1, wherein the one or more errors includes any one or more of:

a measurement of the voltage of a battery in the smoking substitute device;

a measurement of the resistance of a coil in the smoking substitute device;

an indication of the number of times a consumable is inserted into the smoking substitute device within a given period;

an indication of the number of times that the smoking substitute device has failed to connect to a mobile device within a given period;

an indication that there is an issue with charging a battery within the smoking substitute device; and an indication that a pressure within the smoking substitute device has dropped.

8. The method of claim 1, wherein the mobile device selects the updated firmware from a store of firmware stored in memory of a remote server.

9. The method of claim 1, wherein the updated firmware is selected from the multiple items of firmware so as to address the one or more errors encountered by the smoking substitute device.

10. A smoking substitute device, comprising:

a processor; and a memory, wherein the memory includes instructions which cause the processor to:

log one or more error(s) encountered by the smoking substitute device, the one or more errors indicative of a fault in the smoking substitute device;

transmit the one or more errors to a mobile device;

receive from the mobile device an updated firmware suitable for use by the processor of the smoking substitute device, where the updated firmware is selected by the mobile device to address the one or more error(s) encountered by the smoking substitute device; and update firmware of the smoking substitute device with the updated firmware received from the mobile device to prevent or ameliorate at least some of the one or more errors in future use of the smoking substitute device.

11. A computer implemented method for updating firmware of a smoking substitute device, the method comprising the steps of:

logging, by the smoking substitute device, one or more errors encountered by the smoking substitute device;

assessing, by the mobile device, the one or more errors encountered by the smoking substitute device to thereby ascribe a fault in the smoking substitute device to the one or more errors;

the mobile device selecting, from a store of multiple items of firmware suitable for use in the smoking substitute device, based on the assessing performed by the mobile device of the one or more errors encountered by the smoking substitute device, an updated firmware for use by a processor in the smoking substitute device to address the fault;

transmitting, from the mobile device to the smoking substitute device, the updated firmware; and updating the firmware of the smoking substitute device with the updated firmware received from the mobile device to prevent or ameliorate at least some of the one or more errors in future use of the smoking substitute device.

* * * * *